United States Patent
Zhang et al.

(10) Patent No.: US 10,892,050 B2
(45) Date of Patent: Jan. 12, 2021

(54) DEEP IMAGE CLASSIFICATION OF MEDICAL IMAGES

(71) Applicant: International Business Machines Corporation, Armonk, NY (US)

(72) Inventors: Xin Zhang, Beijing (CN); Guo Tong Xie, Beijing (CN); Xiaolu Zhang, Beijing (CN); Xiu Li Li, Beijing (CN); Peng Gao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 176 days.

(21) Appl. No.: 15/952,361

(22) Filed: Apr. 13, 2018

(65) Prior Publication Data

US 2019/0318822 A1 Oct. 17, 2019

(51) Int. Cl.
| | |
|---|---|
| *G06K 9/62* | (2006.01) |
| *G16H 30/40* | (2018.01) |
| *G06N 3/08* | (2006.01) |
| *G06N 3/04* | (2006.01) |

(52) U.S. Cl.
CPC ........... *G16H 30/40* (2018.01); *G06K 9/6257* (2013.01); *G06K 9/6262* (2013.01); *G06K 9/6267* (2013.01); *G06N 3/04* (2013.01); *G06N 3/084* (2013.01); *G06K 2209/05* (2013.01)

(58) Field of Classification Search
CPC ........ G16H 30/40; G16H 50/20; G16H 50/70; G06N 3/084; G06N 3/04; G06K 9/6262; G06K 9/6257; G06K 9/6267; G06K 9/00147; G06K 9/4628; G06K 2209/05
See application file for complete search history.

(56) References Cited

U.S. PATENT DOCUMENTS

| | | | |
|---|---|---|---|
| 9,684,967 B2 | 7/2017 | Abedini et al. | |
| 10,499,857 B1* | 12/2019 | Nguyen | G06N 3/08 |
| 2003/0229278 A1* | 12/2003 | Sinha | G06K 9/6247 |
| | | | 600/407 |

(Continued)

FOREIGN PATENT DOCUMENTS

| | | | |
|---|---|---|---|
| CN | 106803247 A | | 6/2017 |
| CN | 107688815 A | * | 2/2018 |

OTHER PUBLICATIONS

Translated version of CN107688815 (Year: 2018).*

(Continued)

*Primary Examiner* — Carol Wang
(74) *Attorney, Agent, or Firm* — Patterson + Sheridan, LLP

(57) ABSTRACT

Methods, systems, and storage components for utilizing a deep neural network(s) for classifying at least one medical image. A deep neural network (DNN) can be configured by an image processing component to contain at least one revived neuron, where the revived neuron has an adjusted value based on a focus-learning function that is transferred to the DNN by the image processing component, where the focus-learning function provides the adjustment by updating the DNN with data that contains a corrected classification with respect to at least one normal image sample derived from a medical image, and where the correction is based on the focus-learning function comparing an annotation associated with an abnormal image sample derived from the medical image to another annotation associated with the at least one normal image.

24 Claims, 5 Drawing Sheets

(56) References Cited

U.S. PATENT DOCUMENTS

| | | | |
|---|---|---|---|
| 2014/0219548 A1* | 8/2014 | Wels | G16H 30/20 |
| | | | 382/154 |
| 2017/0039689 A1 | 2/2017 | Solanki et al. | |
| 2017/0148166 A1 | 5/2017 | Alpert et al. | |
| 2018/0181867 A1* | 6/2018 | Seibold | G06K 9/6253 |
| 2018/0232601 A1* | 8/2018 | Feng | G06T 7/0004 |
| 2019/0042826 A1* | 2/2019 | Chang | G06K 9/0014 |
| 2019/0156476 A1* | 5/2019 | Yoshida | G06K 9/6269 |
| 2019/0221313 A1* | 7/2019 | Rim | G16H 30/40 |

OTHER PUBLICATIONS

Kooi, Thijs, et al. "A comparison between a deep convolutional neural network and radiologists for classifying regions of interest in mammography." In International Workshop on Breast Imaging, pp. 51-56. Springer, Cham, 2016. (Year: 2016).*

Li, Yuanzhong, Shoji Hara, Wataru Ito, and Kazuo Shimura. "A machine learning approach for interactive lesion segmentation." In Medical Imaging 2007: Image Processing, vol. 6512, p. 651246. International Society for Optics and Photonics, 2007. (Year: 2007).*

Van Grinsven, Mark JJP, Bram van Ginneken, Carel B. Hoyng, Thomas Theelen, and Clara I. Sánchez. "Fast convolutional neural network training using selective data sampling: Application to hemorrhage detection in color fundus images." IEEE transactions on medical imaging 35, No. 5 (2016): 1273-1284. (Year: 2016).*

Russakovsky, Olga, Jia Deng, Hao Su, Jonathan Krause, Sanjeev Satheesh, Sean Ma, Zhiheng Huang et al. "Imagenet large scale visual recognition challenge." International journal of computer vision 115, No. 3 (2015): 211-252. (Year: 2015).*

Kooi, Thijs, Geert Litjens, Bram Van Ginneken, Albert Gubern-Mérida, Clara I. Sánchez, Ritse Mann, Ard den Heeten, and Nico Karssemeijer. "Large scale deep learning for computer aided detection of mammographic lesions." Medical image analysis 35 (2017): 303-312. (Year: 2017).*

* cited by examiner

DEEP IMAGE CLASSIFICATION OF MEDICAL IMAGES

BACKGROUND

1. Field of the Invention

The present invention, in some embodiments thereof, relates to creating a function for classifying images, and, more specifically, but not exclusively, to creating focus-learning functions for classifying medical images objects in association with a deep-neural network (DNN).

2. Related Art

With the increasing need for classifying large volumes of captured and/or extracted media, learning models have become a common practice for classifying the captured media objects. The learning models, such as for example, artificial neural networks (ANN) and/or convolutional neural networks (CNN), are trained with sample data, i.e. sample media objects and continuously evolve (learn) during the process of classifying new (previously unseen) media objects.

SUMMARY

One aspect of the invention includes a computer implemented method of automatically improving classification of at least one medical image. The computer implemented method includes: using at least one hardware processor for executing a code including code instructions for performing the following: extracting a plurality of samples from the at least one medical image, where the plurality of samples includes i) at least one image sample with a normal portion of organic matter and ii) at least one image sample with an abnormal portion of organic matter, training a focus-learning function for an image analysis component with the plurality of samples by comparing a first classification made by the image analysis component as to at least one of i) the at least one normal image sample and ii) the at least one abnormal image sample to at least one annotation associated with at least one of i) the at least one normal image sample and ii) the at least one abnormal image sample, determining that the classification was erroneous based on the annotation, and updating the focus-learning function to reflect a correct classification of at least one of the i) the normal image sample and ii) the abnormal image sample based on the determination that the classification was erroneous.

Another aspect of the invention includes a computer-readable storage media for performing at least one classification operation on at least one medical image. The computer-readable storage media contains computer program code that, when executed by operation of one or more computer processors, performs an operation including: using at least one hardware processor for executing a code including code instructions for performing the following: extracting a plurality of samples from the at least one medical image, where the plurality of samples includes i) at least one image sample with a normal portion of organic matter and ii) at least one image sample with an abnormal portion of organic matter, training a focus-learning function for an image analysis component with the plurality of samples by comparing a first classification made by the image analysis component as to at least one of i) the at least one normal image sample and ii) the at least one abnormal image sample to at least one annotation associated with at least one of i) the at least one normal image sample and ii) the at least one abnormal image sample, determining that the classification was erroneous based on the annotation, and updating the focus-learning function to reflect a correct classification of at least one of the i) the normal image sample and ii) the abnormal image sample based on the determination that the classification was erroneous.

Another aspect of the present disclosure includes a system for performing at least one classification operation on at least one medical image. The system includes one or more computer processors, and a memory containing computer program code that, when executed by operation of the one or more computer processors, performs an operation including: using at least one hardware processor for executing a code including code instructions for performing the following: extracting a plurality of samples from the at least one medical image, where the plurality of samples includes i) at least one image sample with a normal portion of organic matter and ii) at least one image sample with an abnormal portion of organic matter, training a focus-learning function for an image analysis component with the plurality of samples by comparing a first classification made by the image analysis component as to at least one of i) the at least one normal image sample and ii) the at least one abnormal image sample to at least one annotation associated with at least one of i) the at least one normal image sample and ii) the at least one abnormal image sample, determining that the classification was erroneous based on the annotation, and updating the focus-learning function to reflect a correct classification of at least one of the i) the normal image sample and ii) the abnormal image sample based on the determination that the classification was erroneous.

Another aspect of the present disclosure includes a memory component for storing computer executable instructions in a computer device, where the memory component includes: a deep neural network (DNN) configured by an image processing component to contain at least one revived neuron, where the revived neuron has an adjusted value based on a focus-learning function that is transferred to the DNN by the image processing component, where the focus-learning function provides the adjustment by updating the DNN with data that contains a corrected classification with respect to at least one normal image sample derived from a medical image, and where the correction is based on the focus-learning function comparing an annotation associated with an abnormal image sample derived from the medical image to another annotation associated with the at least one normal image.

DETAILED DESCRIPTION

At least one embodiment of the present disclosure improves classification of medical images and samples associated therewith. Medical images depicting micro-abnormalities on organic matter, e.g. a lesion on skin, can be analyzed using image processing techniques and techniques that employ neural networks, including convolving neural networks (CNN) and deep neural networks (DNN). However, since it is likely most medical images of this kind will yield samples with a much higher negative depiction of an abnormality, e.g. do not depict an abnormality, than positively depicting an abnormality, e.g. depicting an abnormality, there is a need to both increase the efficiency of processing such vast sample sizes by having a technique for making conclusive determinations. Moreover, having a technique for making conclusive determinations enhances the accuracy of a machine employing such CNNs or DNNs, enhances the efficiency of such a machine by minimizing computational resources, and improves the field of medical diagnostics by providing a method and system for quickly and automatically producing useful and accurate medical images relevant to a particular medical matter.

Figure 1:
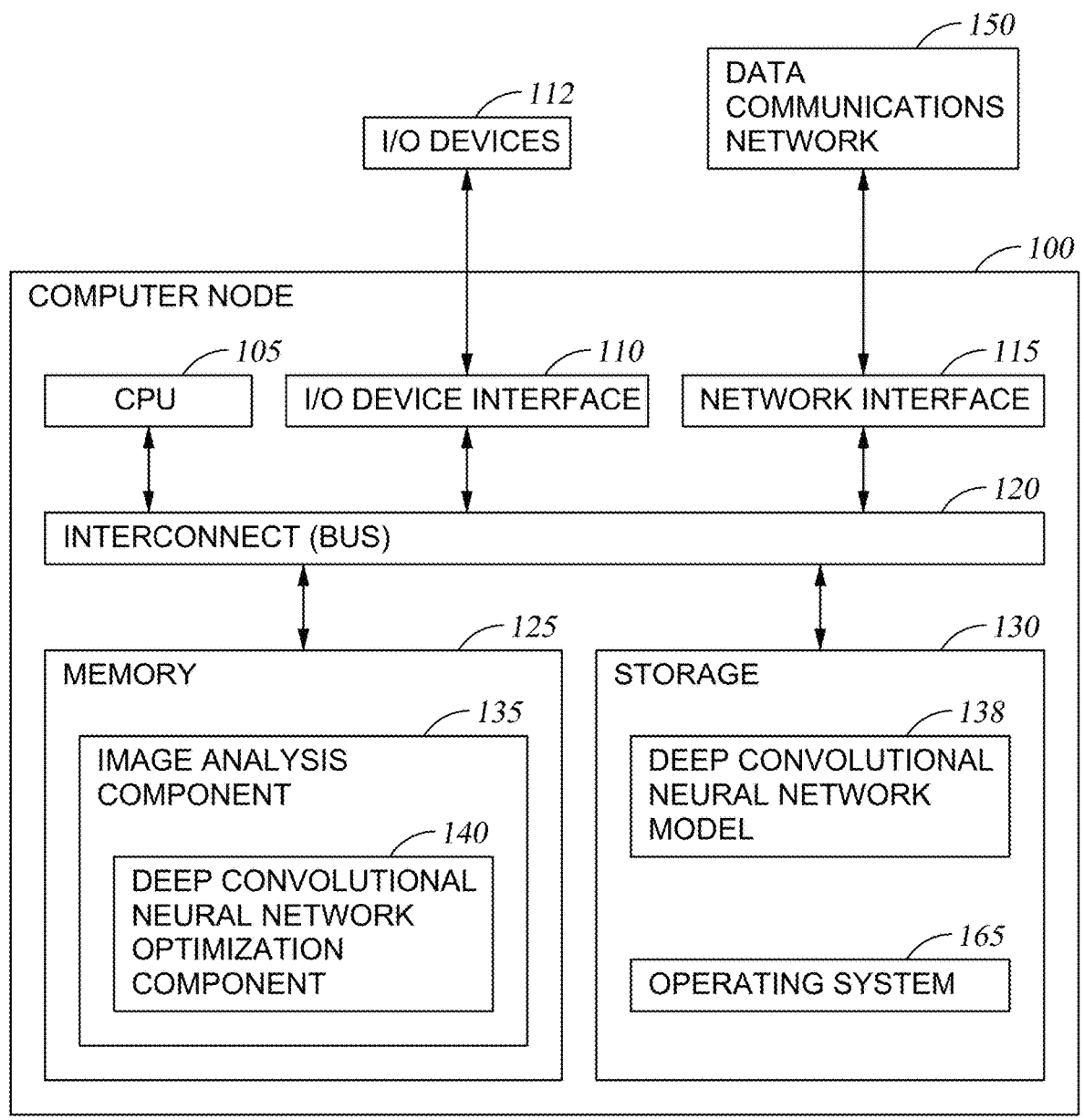
FIG. 1 illustrates a compute node configured with a deep convolutional neural network optimization component, according to at least one embodiment of the present disclosure.

FIG. 1 illustrates a compute node 100, according to one embodiment described herein. The compute node 100 is configured with an image analysis component 135, which further includes a deep convolutional neural network optimization component 140. The compute node 100 can include, without limitation, one or more processors (CPUs) 105, a network interface 115, an interconnect (BUS) 120, a memory 125, and a storage 130. The compute node 100 can also include an I/O device interface 110 used to connect I/O devices 112, e.g., keyboard, display, and mouse devices, to the compute node 100. In some embodiments, the compute node 100 represents a particular compute instance of a single computing device (e.g., computing components within a chassis, a blade within a blade server, an I/O drawer, a processor chip, etc.). Alternatively, the compute node 100 can represent an entire computing device that includes one or more processors and one or more associated memory devices.

Each CPU 105 retrieves and executes programming instructions stored in the memory 125 or storage 130. Similarly, the CPU 105 stores and retrieves application data residing in the memory 125. The interconnect 120 is used to transmit programming instructions and application data between each CPU 105, I/O device interface 210, storage 130, network interface 115, and memory 125. The interconnect 120 can be one or more busses. The CPUs 105 can be a single CPU, multiple CPUs, or a single CPU having multiple processing cores in various embodiments. In one embodiment, a processor 105 can be a digital signal processor (DSP).

The memory 125 is generally included to be representative of a random access memory, e.g., Static Random Access Memory (SRAM), Dynamic Random Access Memory (DRAM), or Flash. The storage 130 is generally included to be representative of a non-volatile memory, such as a hard disk drive, solid state device (SSD), or removable memory cards, optical storage, flash memory devices, network attached storage (NAS), or connections to storage area network (SAN) devices, or other devices that can store non-volatile data. The network interface 115 is configured to transmit data via the communications network 150.

The compute node 100 can include one or more operating systems. An operating system can be stored partially in memory 125 and partially in storage 130. Alternatively, an operating system can be stored entirely in memory 125 or entirely in storage 130. The operating system provides an interface between various hardware resources, including the CPU 105, I/O device interface 110, network interface 115 and so on. In addition, an operating system provides common services for application programs, such as providing a time function.

Figure 3A:
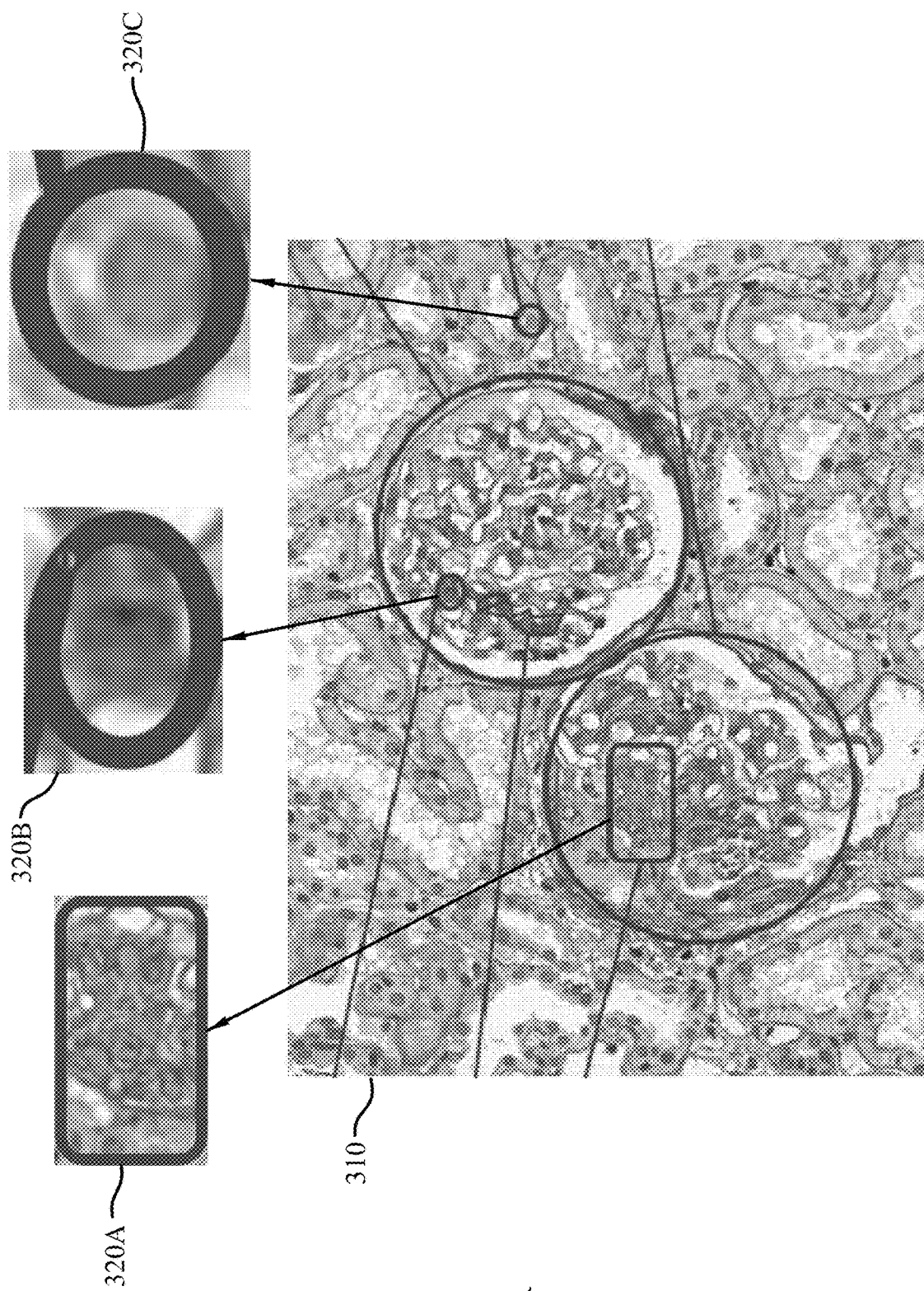
FIG. 3A illustrates a medical image suitable for use with at least one embodiment of the present disclosure.
Figure 3B:
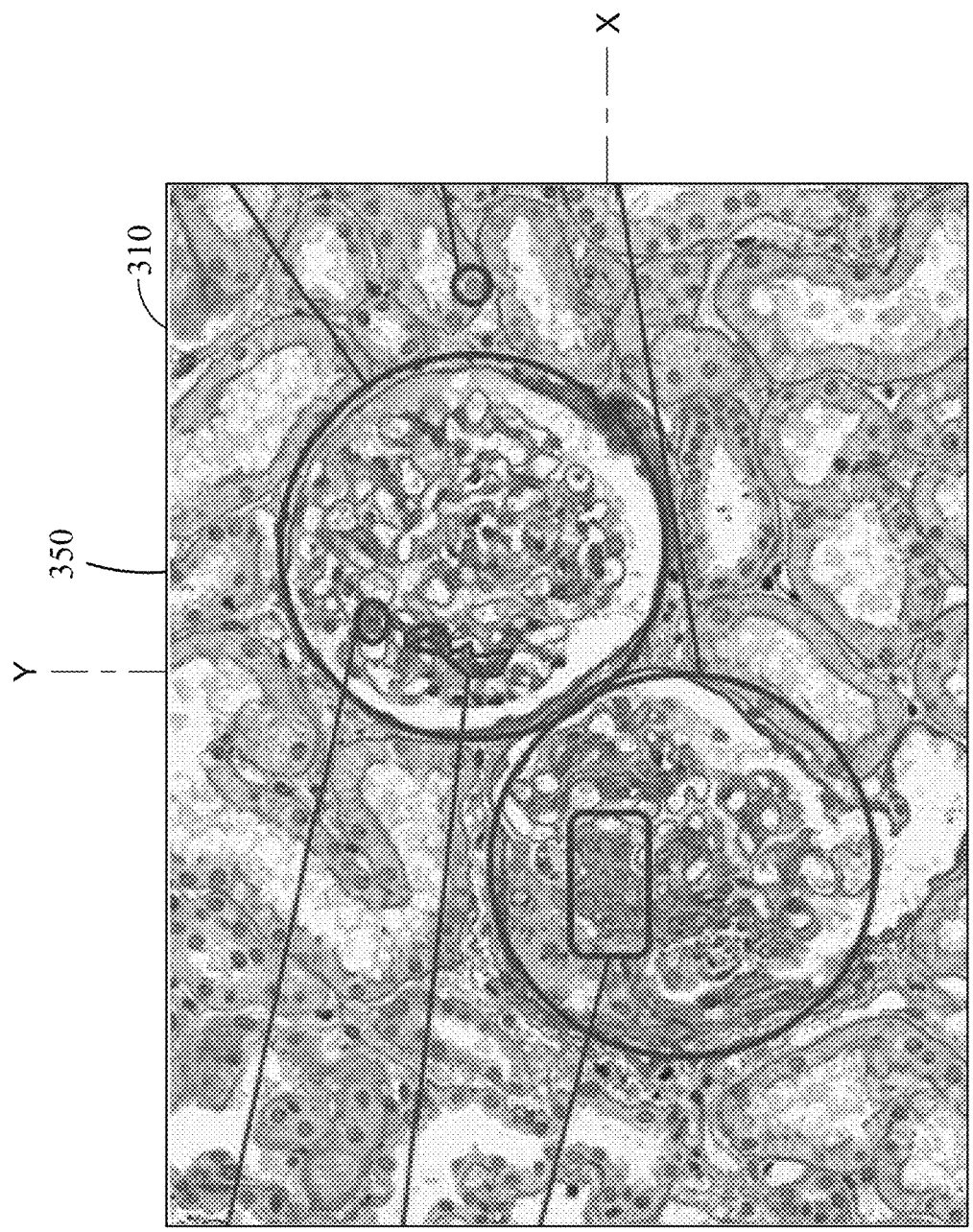
FIG. 3B illustrates a medical image suitable for use with at least one embodiment of the present disclosure.

The image analysis component 135 can be configured to perform a variety of tasks, including, with the DCNN optimization component 140, establishing a classification function, e.g. a focus-learning function, for one or more medical images, such as the image shown in FIG. 3A and FIG. 3B. Suitable models that can be employed in this scheme include neural networks, for example, a model based on a convolutional neural network (CNN) such as a deep neural network (DNN), including a deep convolutional neural network (DCNN). In one embodiment, the process for creating the classification function(s) or focus-learning function(s) involves a deep learning process during which a plurality of features or samples, e.g. patches, are extracted from one or more medical images, and the features are used to create one or more feature maps and training the classification function(s) or focus-learning function(s) with the feature map(s).

The first step in creating the classification function(s) is feature extraction. Each of the extracted features may be an individual property of the one or more medical images, e.g. a patch of the one or more medical images. The plurality of features, e.g. patches, of the medical image, is extracted during a learning process of a CNN model processing to create one or more feature maps. The CNN model may include one or more convolutional layers with pooling layers inserted in between them. The pooling layers are inserted to reduce the amount of data that is processed by the successive convolution layer thus reducing processing load and/or processing time. Each of the convolutional layers may include a plurality of learnable filters (kernels) each having a weight and a bias which are small (smaller than the input sample media object). Each of the filters is applied to sub-regions of each of the one or more medical images and is replicated over the entire contents of each of the input sample media objects. Each of the filters may be learned to activate at the detection of one or more features, e.g. patches, within the one or more medical images to compute a dot product. The filters may be incorporated with a non-linearity module, for example, a rectified linear unit (ReLU) to apply non-linearity to each bit in convolved data of the filter. Stacking together the activation points of the filters may form the complete activation map and/or feature map of the convolutional layer of the CNN model for each of the features. Following the entire path of CNN model the feature map(s) may be further extended for mapping each of the plurality of features detected in the sample media objects.

The deep convolutional neural network (DCNN) optimization component 140 is generally configured to optimize the structure of the trained DCNN model 138. In order to achieve a balance between the predictive power and model redundancy of CNNs, the DCNN optimization component 140 can learn the importance of convolutional kernels and neurons in FC layers, convolutional layers, or any other suitable layer, from a feature selection perspective. The DCNN optimization component 140 can optimize a CNN by updating weights associated with particular kernels that correspond to patches associated with one or more medical images. Specifically, in one embodiment, the DCNN optimization component 140 can assign a weight to a kernel or update a weight of a kernel based on the image analysis component 135 determining that a particular patch or sample of the one or more medical images was erroneously classified as containing an abnormality in association with a piece of organic matter, e.g. a lesion on skin or an organ.

The image analysis component 135 can compare a classification determination with respect to an image sample with an annotation, and determine that the classification was incorrect, where such as determination is considered a "hard negative" determination. The image analysis component can then compile a data set including a plurality of hard negative determinations that the DCNN optimization component 140 can use to adjust the weights of kernels associated with the image samples corresponding to those plurality of hard negative determinations. In one embodiment, the image analysis component 135 can create a data set consisting of all or essentially all hard negative determinations and/or hard negative determinations and positive determinations, where the latter refers to determinations that correctly classified a sample as belonging to an abnormal organic matter, and forward it to the DCNN optimization component 140, which in turn will use the data set to update and optimize the DCNN model 138.

In one embodiment, the DCNN optimization component 140 can fine-tune the remaining kernels and neurons to achieve a minimum loss of accuracy in the optimized DCNN model 138. To measure importance scores over the entire DCNN model 138 efficiently and consistently, the DCNN optimization component 140 can utilize a back propagation technique or other suitable output to input analysis, which enables one-time feature ranking on a high-level layer of the DCNN and back propagates the importance calculations to the lower layers of the DCNN. These techniques can also determine which neurons in the network are dead, e.g. have a starting weight so high or low or are otherwise are arranged in the network so as to never be activated. Back-propagation or another suitable technique can allow the DCNN optimization component 140 to update the DCNN model 138 by reviving dead neurons that are associated with hard negative sample images and/or sample images that share similar characteristics to hard negative sample images.

Figure 2:
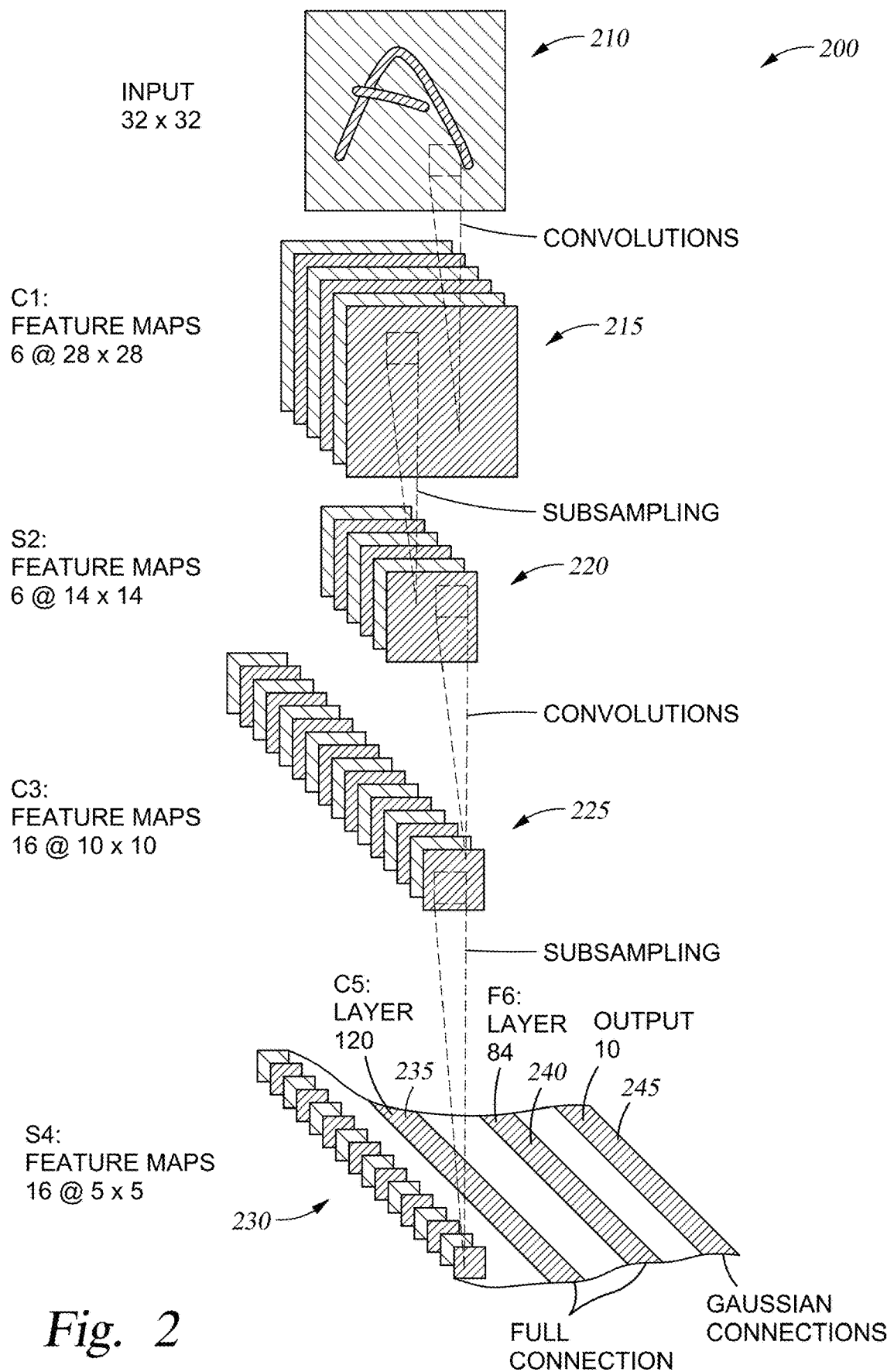
FIG. 2 illustrates a convolutional neural network, according to at least one embodiment of the present disclosure.

FIG. 2 illustrates a convolutional neural network 200, according to one embodiment described herein. As shown, the CNN 200 includes an input layer 210, e.g. one or more medical images, a convolutional layer 215, a subsampling layer 220, a convolutional layer 225, subsampling layer 230, fully connected layers 235 and 240, and an output layer 245. The input layer 210 in the depicted embodiment is configured to accept a 32×32 pixel image. The convolutional layer 215 generates 6 28×28 feature maps from the input layer, and so on. While a particular CNN 200 is depicted, more generally a CNN is composed of one or more convolutional layers, frequently with a subsampling step, and then one or more fully connected layers. Generally, the CNN architecture is designed to take advantage of the two-dimensional structure of an input image (or other two-dimensional input, e.g., a speech signal). For example, CNNs may achieve these using local connections and tied weights followed by some form of pooling, resulting in translation invariant features. Generally, CNNs may be easier to train and tend to have fewer parameters, relative to fully connected networks with a similar number of hidden units. It should be noted that this model is provided for instructive purposes only, and other models can be applied, provided the model can accommodate at least one technique in accordance with the present disclosure, e.g. applying a technique which considers hard negative and/or positive results (discussed below) to make a classification or determination.

Generally, a CNN includes convolutional and subsampling layers, which may be followed by fully connected layers. According to one embodiment, the CNN 200 is configured to accept an x by y by z image as input at a convolutional layer of the CNN 200, where x and y represent the height and width of the image, and z represents the number of channels in the image. For example, an RGB image would have z=3 channels. The convolutional layer may include k filters (or kernels) of size a by b by c, where a by b is smaller than x by y, and c is less than or equal to z (and may vary for various kernels). Generally, the size of filters k leads to a locally connected structure, which is convolved with the image to produce k feature maps. Additionally, each map can be subsampled over contiguous regions of various sizes (e.g., 2×2 may be appropriate for small images, while up to 5×by 5 may be appropriate for larger images). In some embodiments, an additive bias and sigmoidal nonlinearity is applied to each feature map (e.g., prior or subsequent to the subsampling layer). Any number of fully connected layers may follow the convolutional layers.

As discussed above, conventional CNNs consist of convolutional (Cony) layer, pooling layer, non-linear layer (e.g. ReLU), normalization layer (e.g. local response normalization (LRN)) and fully connected (FC) layer, etc. The convolutional layer generally includes a set of trainable kernels, which extract local features from a small spatial region but cross-depth volume of the input tensor. Each kernel can be trained as a feature extractor for some specific visual features, such as an edge or a color in the first layer, or a paw-like or ball-like pattern in higher layers. In FC layers, neurons can be fully connected to all activations in the previous layer. Although an end-to-end CNN can solve a classification task directly by mapping an input to a probability distribution over all classes, intermediate features from FC layers or Cony layers can be extracted to train other specific classifiers. According to one or more techniques provided herein, any suitable layer disclosed herein or otherwise known can be used in accordance with the teachings of the present disclosure, e.g. applying a technique which considers hard negative and/or positive results (discussed below) to make a classification or determination.

The DCNN optimization component 140 can perform Importance Score Back Propagation (ISBP) or another suitable technique to update an existing CNN, including a DCNN, to reactivate dead neurons or otherwise update the DCNN model 138 based on the focus-learning function. In one embodiment, the DCNN optimization component 140 can apply feature ranking on higher level features of the CNN, e.g. the inputs of the classifier. The DCNN optimization component 140 can then back-propagate the importance scores to the lower layers of the CNN. Through the use of ISBP, the DCNN optimization component 140 can efficiently measure the importance of feature extractors of an entire deep neural network and can do so consistently across the network.

FIG. 3A and FIG. 3b illustrate a medical image 310 that can serve as an input 210 for a CNN, including a DCNN. In one embodiment, a base line DCNN model 138 is formed by the image analysis component 140 parsing the image into various sub-sections or sample images, e.g. 320A, 320B, and 320C. Note, that three samples are shown here for convenience, as a CNN, and especially a DCNN, can have orders of magnitude more images as inputs and more samples associated with each image. The parsing and classifying technique can be as provided for herein or as provided for in U.S. Pat. No. 9,684,967B2 entitled "Imaging segmentation using multi-scale machine learning approach," the entirety of which is incorporated herein by reference. In assigning weights in the model, the base-line model can have weights assigned to various kernels or neurons associated with particular sample images, where the weights can consider various features, such as appearance to previously classified images, human input, etc. In one embodiment, assigned weights may not account for a scenario where a hard negative result has taken place. A hard negative result occurs when the DCNN model classifies a sample as being associated with a portion of the one or more medical images, e.g. 310, that has an abnormality on organic matter, e.g. a lesion on skin or an organ, but an annotation or other conclusive indicator determines that that classification is erroneous. For example, as depicted in FIG. 3B, the one or more medical images 310 may be associated with Cartesian coordinates and a boundary box 350 that defines the region will be associated with that region. A focus learning function implemented by the image analysis component 135 can compare the coordinates of the classified image with the coordinates of the boundary box, and if there is no overlap, it can be conclusively determined a mistaken classification has occurred. Since there usually will be orders of magnitude more negative samples than positive samples, e.g. because lesions and other small abnormalities on organic matter will be confined to small spaces on the medical image 310, without the same frequency as normal tissue or matter, reclassifying false positive can significantly enhance the accuracy of the DCNN model 138.

Although the above embodiment uses Cartesian coordinates to make a firm false classification determination, other annotations can work as well, including but not limited to direct human input or text-recognition techniques that can determine that the one or more medical images 310 are not associated with an abnormality. The boundary box 350 that provides for the area for a sample, e.g. 320A, that is associated with an abnormality can be provided by any suitable boundary defining technique and/or human input.

The image analysis component 135 can output the determinations as to hard negative classifications and positive classifications, e.g. instances where the coordinates match to the coordinate associated with an abnormality or human input indicates that a particular sample is associated with an abnormality. The image analysis component 135 can supplement this data with random or guided sampling of other images samples of the medical image 310, including negative determinations that are not confirmed as hard negative, hard negative determinations and positive determinations. For example, for simplicity sake, 320A qualifying as a positive, 320B qualifying as a hard negative, and 320C as a negative determination without subsequently confirmation of the correctness of that determination. In one embodiment, to enhance accuracy, the image analysis component can specifically search for only one of or both hard negative and positive determinations, and provide that data set to the DCNN optimization component 140 in order to maximize accuracy. Based on this data, the DCNN optimization component 140 can transfer the focus-learning function to the DCNN 138 or otherwise update the DCNN 138 so it has more accurate weights for classification.

Figure 4A:
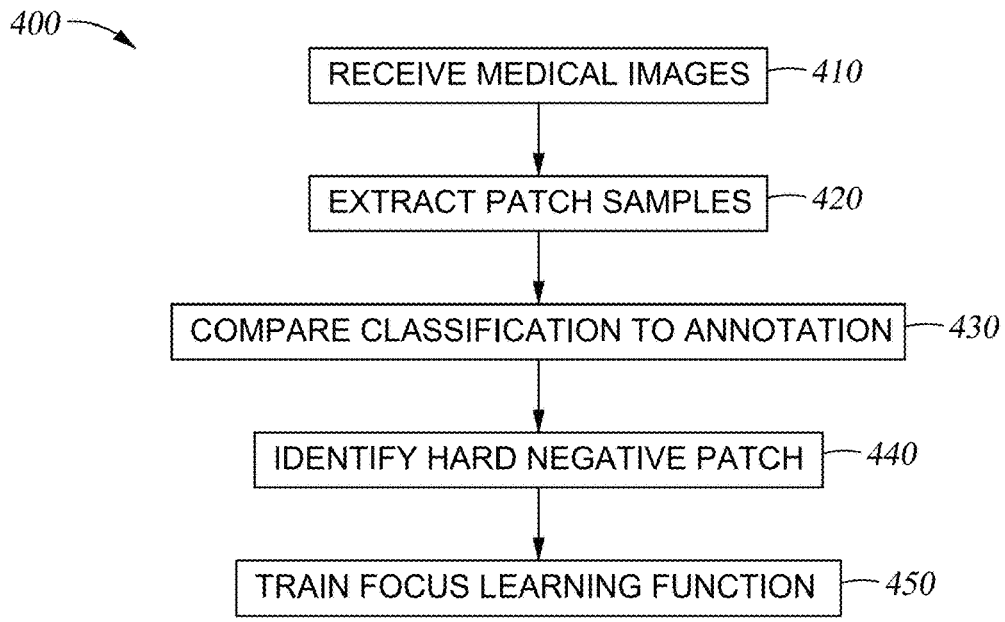
FIG. 4A is a flow diagram illustrating a method of classifying a medical image in accordance with at least one embodiment of the present disclosure.

FIG. 4A is a flow diagram illustrating a method 400 of utilizing a focus-learning function to enhance medical image classification, according to one embodiment described herein. As shown, the method 400 begins at block 410, where the image analysis component 135 receives one or more medical images, e.g. 310. In block 420, the image analysis component 135 performs a sampling partition of the medical image 410 in accordance with the techniques discussed herein or as otherwise are known and appropriate for use in neural networks generally, and deep neural networks specifically. In block 430, the image analysis component 135 communicates with the DCNN optimization component 140 and identifies a trained CNN, e.g. 138, that has processed and classified the medical image with the same or similar partition. The image analysis component 135 identifies kernels or neurons associated with samples that have a negative classification, and compares annotations associated with those negatively classified samples and conclusively positive, e.g. conclusively abnormal samples. The image analysis component 135 has compiled this data, and transfers the data to the DCNN optimization component 140 that will rebuild the classifier assigning weights in the DCNN network 138 and/or otherwise ensure that the network 138 is modified pursuant to a focus-learning or classification function that accounts for the new data.

In one embodiment, at block 440, all hard negative classifications are compiled and determined by the image analysis component 135, and constitute the exclusive data set that will form the basis for the DCNN optimization component 140 updating the DCNN 138. In another embodiment, the data set is mixed in with positive classifications, and in another embodiment random sampling is employed and the data set includes negative classifications whose veracity has not been confirmed.

At block 450, the focus-learning function is developed by the DCNN optimization component 140 and transferred to the DCNN 138. In one embodiment, the focus-learning function can be transferred to a different deep cognitive neural network that has similar content as DCNN 138 because samples that resemble samples with a hard negative classification and/or a positive classification can be assigned a higher or lower weight, even if they are not associated with a same medical image.

Figure 4B:
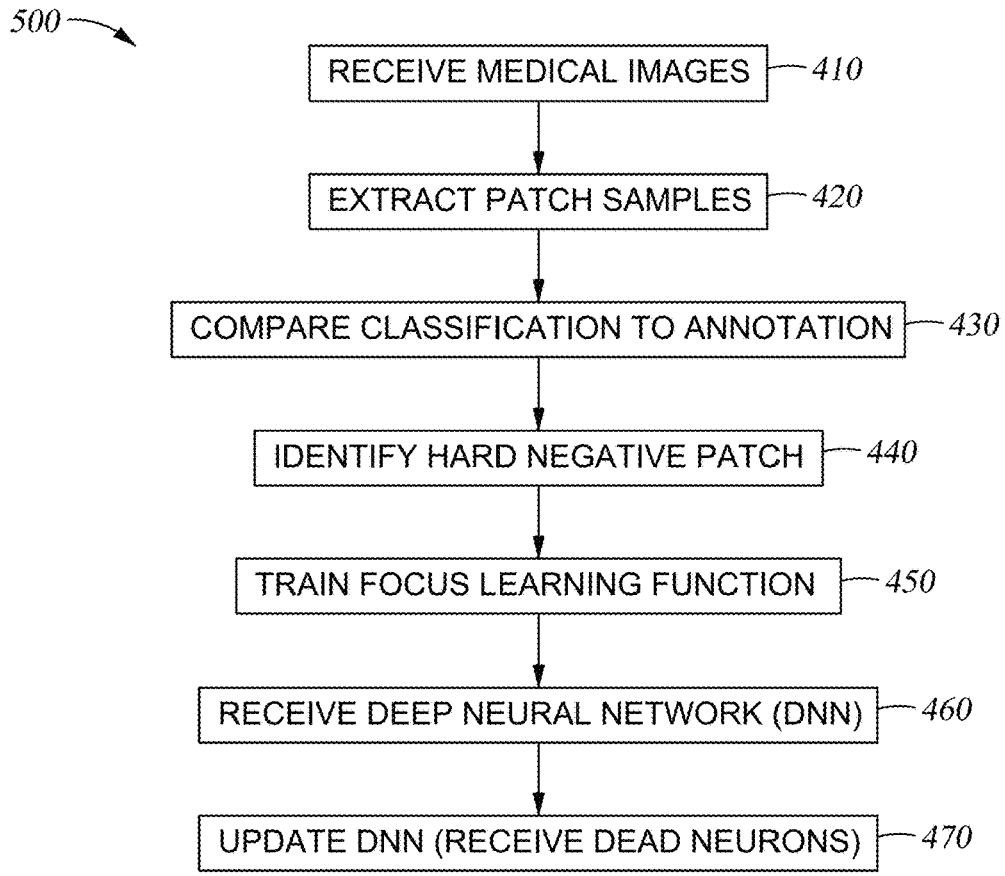
FIG. 4B is a flow diagram for improving a deep-neural network in accordance with at least one embodiment of the present disclosure.

FIG. 4B illustrates a method 500 for enhancing the classification accuracy associated with a DCNN, e.g. 138. In one embodiment, the focus-learning function, configured by the DCNN optimization component 140, can revive dead neurons of a DCNN, e.g. 138. At block 460, the DCNN 138 is received or engaged by the DCNN optimization component 140, and at block 470, one or more kernels or neurons associated with an extreme erroneous weight (e.g., a weight that is below a minimum weight threshold) that is assigned thereto based on a misclassification, thus causing the neuron or kernel to be completely excluded during convolution or other operations, can be reactivated as a result of the focus learning function that accounts for firm determinations, e.g. hard negatives and positives.

In the present disclosure, reference is made to various embodiments. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the described aspects, features, embodiments and advantages are merely illustrative and are not considered elements or limitations of the appended claims except where explicitly recited in a claim (s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A computer implemented method for improving classification of a medical image comprising:
    extracting, by a processor, a plurality of samples from the medical image, wherein the plurality of samples includes a normal image sample of a normal portion of organic matter;
    training a focus-learning function for an image analysis component with the plurality of samples by:
        generating a classification by processing the normal image sample using the image analysis component;
        determining that the classification was erroneous based on an annotation associated with the normal image sample; and
        updating the focus-learning function to reflect a correct classification of the normal image sample based on the determination that the classification was erroneous; and
    updating a deep-neural network (DNN) based on the focus-learning function, wherein the DNN includes a first dead neuron associated with the normal image sample.

2. The computer implemented method of claim 1, wherein the plurality of samples further includes an abnormal image sample of an abnormal portion of organic matter, wherein the abnormal portion of organic matter comprises a lesion on organic tissue, and wherein the normal portion of organic matter comprises organic tissue without a lesion.

3. The computer implemented method of claim 1, the method further comprising identifying a first set of coordinates that identify a location on the medical image associated with an abnormal portion of organic matter.

4. The computer implemented method of claim 3, wherein the classification erroneously indicates that the normal image sample is abnormal, and wherein determining that the classification was erroneous based on the annotation further comprises:
    comparing the first set of coordinates to a second set of coordinates, wherein the second set of coordinates are associated with the normal image sample; and
    determining, based on the coordinate comparison, that the first classification was erroneous.

5. The computer implemented method of claim 4, wherein updating the focus-learning function to reflect a correct classification of the normal image sample based on the determination that the classification was erroneous comprises:
    updating the focus-learning function to reflect the correct classification based on the coordinate comparison.

6. The computer implemented method of claim 1 further comprising:
    receiving the DNN, wherein the DNN was trained based on the extracted plurality of samples.

7. The computer implemented method of claim 6, wherein the DNN includes a plurality of dead neurons related to the extracted plurality of samples.

8. The computer implemented method according to of claim 7, further comprising:
    reviving the first dead neuron based on the updated focus-learning function.

9. A non-transitory computer-readable storage medium containing computer program code which, when executed by operation of one or more computer processors, performs an operation comprising:
    extracting a plurality of samples from a medical image, wherein the plurality of samples includes a normal image sample of a normal portion of organic matter;
    training a focus-learning function for an image analysis component with the plurality of samples by:
        generating a classification by processing the normal image sample using the image analysis component;
        determining that the classification was erroneous based on an annotation associated with the normal image sample; and
        updating the focus-learning function to reflect a correct classification of the normal image sample based on the determination that the classification was erroneous; and
    updating a deep-neural network (DNN) based on the focus-learning function, wherein the DNN includes a first dead neuron associated with the normal image sample.

10. The computer-readable storage medium of claim 9, wherein the plurality of samples further includes an abnormal image sample of an abnormal portion of organic matter, wherein the abnormal portion of organic matter refers to a lesion on organic tissue, and wherein the normal portion of organic matter refers to organic tissue without a lesion.

11. The computer-readable storage medium of claim 9, the operation further comprising identifying a first set of coordinates that identify a location on the medical image associated with an abnormal portion of organic matter.

12. The computer-readable storage medium of claim 11, wherein the classification erroneously indicates that the normal image sample is abnormal, and wherein determining that the classification was erroneous based on the annotation further comprises: comparing the first set of coordinates to a second set of coordinates, wherein the second set of coordinates are associated with the normal image sample; and based on the coordinate comparison, determining that the classification was erroneous.

13. The computer-readable storage medium of claim 12, wherein updating the focus-learning function to reflect a correct classification of the normal image sample based on the determination that the classification was erroneous comprises:
    updating the focus-learning function to reflect the correct classification based on the coordinate comparison.

14. The computer-readable storage medium of claim 9, the operation further comprising:
    receiving the DNN, wherein the DNN was trained based on the extracted plurality of samples.

15. The computer-readable storage medium of claim 14, wherein the DNN includes a plurality of dead neurons related to the extracted plurality of samples.

16. The computer-readable storage medium of claim 15, the operation further comprising:
    reviving the first dead neuron based on the updated focus-learning function.

17. A system comprising:
    one or more computer processors; and a memory containing computer program code that, when executed by operation of the one or more computer processors, performs an operation comprising:
 extracting a plurality of samples from a medical image, wherein the plurality of samples includes a normal image sample of a normal portion of organic matter;
 training a focus-learning function for an image analysis component with the plurality of samples by:
  generating a classification by processing the normal image sample using the image analysis component;
  determining that the classification was erroneous based on an annotation associated with the normal image sample; and
  updating the focus-learning function to reflect a correct classification of the normal image sample based on the determination that the classification was erroneous; and
 updating a deep-neural network (DNN) based on the focus-learning function, wherein the DNN includes a first dead neuron associated with the normal image sample.

18. The system according to claim 17, wherein the plurality of samples further includes an abnormal image sample of an abnormal portion of organic matter, wherein the abnormal portion of organic matter refers to a lesion on organic tissue, and wherein the normal portion of organic matter refers to organic tissue without a lesion.

19. The system according to claim 17, the operation further comprising identifying a first set of coordinates that identify a location on the medical image associated with an abnormal portion of organic matter.

20. The system according to claim 19, wherein the classification erroneously indicates that the normal image sample is abnormal, and wherein determining that the classification was erroneous based on the annotation further comprises:
 comparing the first set of coordinates to a second set of coordinates, wherein the second set of coordinates are associated with the normal image sample; and
 based on the coordinate comparison, determining that the classification was erroneous.

21. The system according to claim 20, wherein updating the focus-learning function to reflect a correct classification of the normal image sample based on the determination that the classification was erroneous comprises:
 updating the focus-learning function to reflect the correct classification based on the coordinate comparison.

22. The system of claim 17, the operation further comprising:
 receiving the DNN, wherein the DNN was trained based on the extracted plurality of samples.

23. The system medium of claim 22, wherein the DNN includes a plurality of dead neurons related to the extracted plurality of samples.

24. The system 23, the operation further comprising:
 reviving the first dead neuron based on the updated focus-learning function.

* * * * *